United States Patent [19]

Tamura et al.

[11] 4,345,150
[45] Aug. 17, 1982

[54] METHOD AND APPARATUS FOR MEASURING THE MOISTURE CONTENT OF PAPER

[75] Inventors: Hisashi Tamura; Naozo Taniguchi; Hirotoshi Ishikawa, all of Tokyo, Japan

[73] Assignee: Yokogawa Electric Works, Ltd., Tokyo, Japan

[21] Appl. No.: 148,808

[22] Filed: May 12, 1980

[30] Foreign Application Priority Data

May 21, 1979 [JP] Japan ................................. 54-63362

[51] Int. Cl.³ .............................................. G01J 1/00
[52] U.S. Cl. ..................................... 250/339; 250/341
[58] Field of Search .................... 356/72, 73; 250/341, 250/349, 350, 339, 340, 351

[56] References Cited

U.S. PATENT DOCUMENTS 3,551,678 12/1970 Mitchell ............................. 250/341
4,097,743 6/1978 Carlson .............................. 250/339

FOREIGN PATENT DOCUMENTS

2044443 10/1980 United Kingdom ............... 250/339

Primary Examiner—Davis L. Willis
Assistant Examiner—Carolyn E. Fields
Attorney, Agent, or Firm—Parmelee, Bollinger & Bramblett

[57] ABSTRACT

Method and apparatus for generating signals corresponding to the moisture content of paper by irradiating a sheet of paper with a near infrared ray, by detecting a beam having a coaction with the paper and by accomplishing the desired arithmetic operations with the use of the detected signals. According to the method and apparatus, at least two optical systems having different degrees of coactions with the paper are provided to respectively detect photometric optical signals and reference optical signals so that the signals corresponding to the moisture content may be generated with the use of the photometric and reference optical signals.

4 Claims, 13 Drawing Figures

METHOD AND APPARATUS FOR MEASURING THE MOISTURE CONTENT OF PAPER

BACKGROUND OF THE INVENTION

The present invention relates to method and apparatus for measuring the characteristics of a sheet-shaped article, and more particularly to method and apparatus for generating the signals having a relationship with the quantity of moisture, which is contained or absorbed in the article, by irradiating the article with a near infrared ray and by detecting the infrared ray having a coaction with that article.

As the sheet-shaped article, for example, paper in a paper machine or a coater is exemplified. One of the indispensable items for administering the quality of the paper is the moisture content measurement in the paper.

Figure 1:
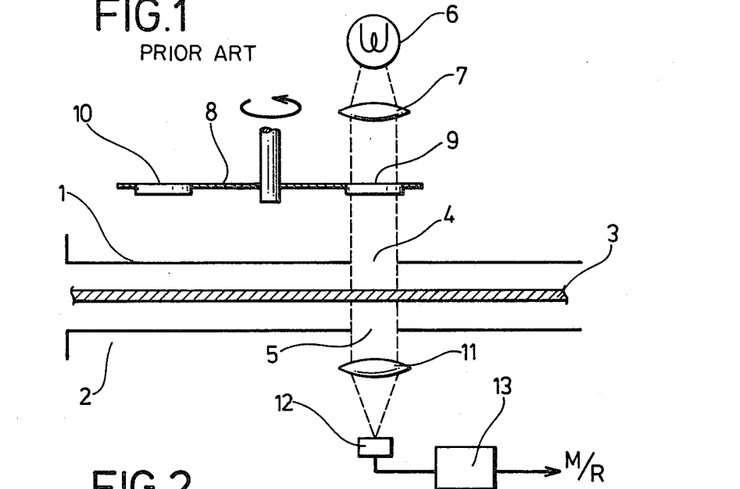
FIG. 1 is an explanatory view illustrating the construction of the detecting unit of a transparent type moisture content meter according to the prior art.
Figure 2:
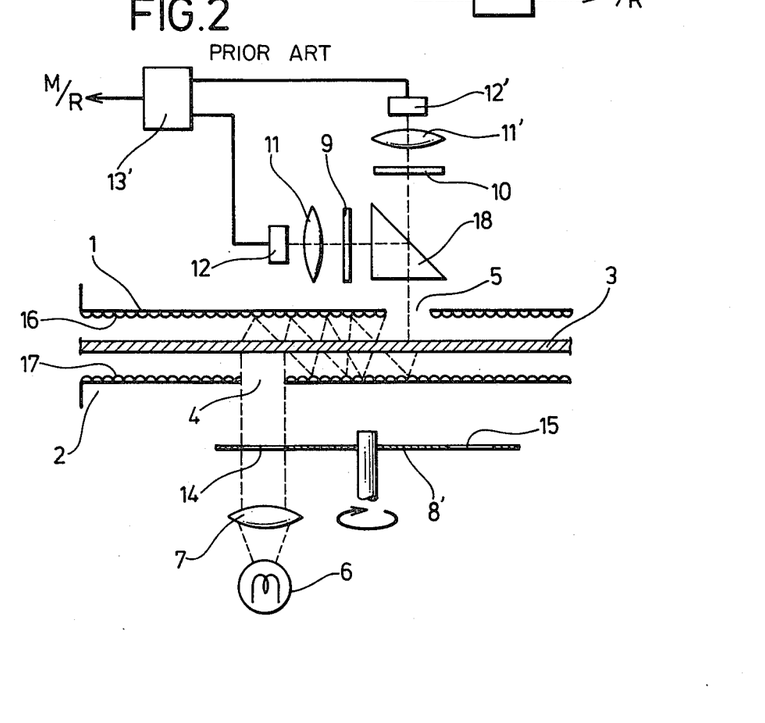
FIG. 2 is similar to FIG. 1 but shows a multi-scattering type moisture content meter according to the prior art.

FIGS. 1 and 2 are diagrammatical views illustrating the constructions of the known moisture content meters for measuring the moisture contents in the above-specified paper, and FIG. 1 is directed to that of transparent type whereas FIG. 2 is directed to that of multi-scattering type.

In FIG. 1, upper and lower heads 1 and 2 are arranged to face each other such that the upper one 1 constitutes an irradiating unit whereas the lower one 2 constitutes a detecting unit. A sheet of paper 3 is interposed between the upper and lower heads 1 and 2 and is irradiated through an irradiation aperture 4 with an interrupted light of the parallel beam, which is prepared by a lamp 6, a lens 7 and a rotary wheel 8 (or a disc-shaped member formed with a through hole). The light having conducted an interaction with the paper 3 and reached an incident aperture 5 is so condensed by a lens 11 that it is detected by a photosensitive element 12. In the construction thus far described, the optical axis of the optical system of the irradiating unit is substantially aligned with that of the optical axis of the detecting unit. On the other hand, the rotary wheel 8 is formed in substantially symmetrical positions with respect to the axis of rotation thereof with the two through holes, in which a photometric optical filter 10 and a reference optical filter 9 are mounted, respectively. As a result, by the afore-mentioned interrupted light, the paper 3 is alternately irradiated with the light having such a wavelength as is determined by the optical filter 10 (or an infrared ray having a wavelength of about 1.95 microns, which will be called the photometric light) and with the light having such a wavelength as is determined by the optical filter 9 (or an infrared ray having a wavelength of about 1.80 microns, which will be called the reference light). Thus, by the action of the photosensitive element 12, the measurement signals (which are generated to correspond to the photometric light and will be called the M signals) and the reference signals (which are generated to correspond to the reference light and will be called the R signals) are detected in a time-series manner and are fed to an arithmetic unit 13. This arithmetic unit 13 is made to have a function of storing an input and a function of accomplishing a dividing operation thereby to generate M/R signals. These M/R signals are fed to a (not-shown) arithmetic unit of the next stage so that they are subjected to the desired arithmetic operation to generate signals corresponding to the moisture content of the paper. In the construction thus described, the reason why the M/R signals are generated is because the characteristic instabilities of the respective components are to be compensated. By taking the ratio between the M signals and the R signals, more specifically, the influences from the agings and the temperature changes of the lamp 6 or the photosensitive element 12 can be eliminated.

Now, the construction of FIG. 2 will be described in the following.

In the facing arrangement of the upper and lower heads 1 and 2 constituting the irradiating and detecting units, the construction of FIG. 2 is characterized in that the irradiation aperture 4 and the incident aperture 5 are offset from each other and in that the upper and lower heads 1 and 2 have their facing surfaces formed with reflective coating films 16 and 17. As a result, the interrupted light, which is prepared by the lamp 6, the lens 7 and a rotary wheel 8' (which is not equipped with any optical filter, as is different from the construction of FIG. 1), reaches the incident aperture 5 after repeated reflection between the paper 3 and reflective surface 16 and 17. The light thus having reached the incident aperture 5 is divided by an optical divider 18 into two lights, one of which is introduced into an M signal system composed of the optical filter 10, a lens 11' and a photosensitive element 12' but the other of which is introduced into an R signal system composed of the optical filter 9, the lens 11 and the photosensitive element 12. The R signals and the M signals, which are detected by the photosensitive elements 12 and 12', occur simultaneously and are fed, as they are, to an arithmetic unit 13' so that they are subjected to a dividing operation to generate the M/R signals.

Now, the water content measuring operations of paper will be described with the use of the respective system having the aforementioned constructions.

Figure 3:
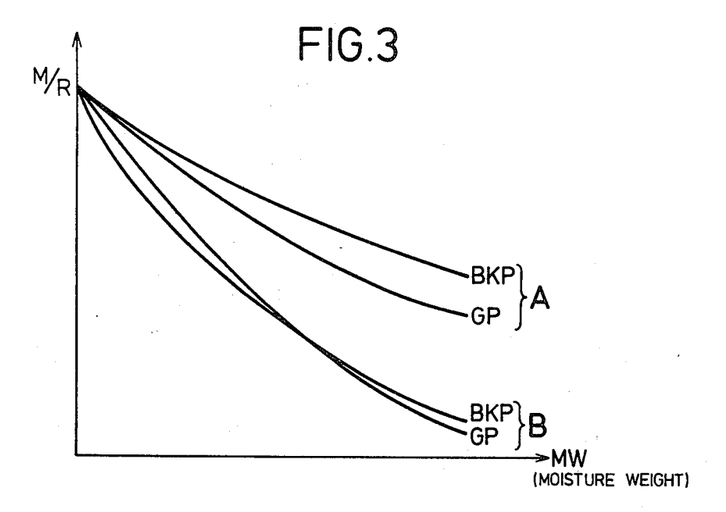
FIGS. 3 and 4 are characteristic curves of the moisture contents of different brands of paper.
Figure 4:
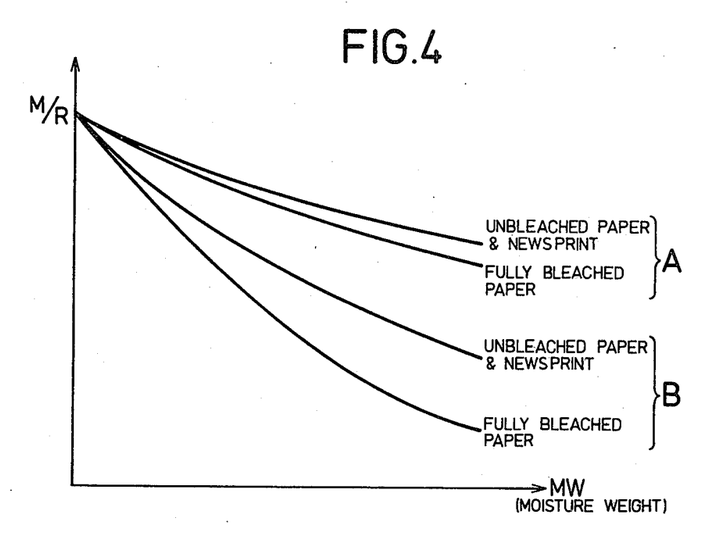

FIG. 3 shows the characteristic curves of GP paper (which is composed mainly of mechanical pulp) and BKP paper (or bleached kraft paper which is composed mainly of chemical pulp). In FIG. 3, curves A are obtained by a transparent type moisture content meter whereas curves B are obtained by a multi-scatter type moisture content meter. On the other hand, FIG. 4 shows the characteristic curves of unbleached paper, newsprint and fully bleached paper, and curves A and B indicate similar recognitions to those of the above. In FIGS. 3 and 4, ordinates indicate the M/R signals (in percentage scale) whereas abscissas indicate the water content MW (in g/m$^2$ scale).

First referring to FIG. 3, the characteristics of the BKP paper and the GP paper are considerably different, as seen from the curves A, but are little different, as seen from curves B. In view of FIG. 4, on the contrary, the characteristics of the unbleached paper, the newsprint (containing deinked pulp) and the fully bleached paper are substantially identical, as seen from the curves A. As seen from the curves B, however, the characteristics of the unbleached paper and the newsprint are found quite different from those of the fully bleached paper.

According to the moisture content meter of the prior art, therefore, the M/R signals, i.e., the moisture content signals are influenced by the mixture ratio of paper materials or by the optical conditions or paper, e.g., the whiteness, the base weight or the pressure applied. In order to lighten and eliminate those influences, the operator of a paper machine or a coater changes the constant of a moisture content calculating equation in accordance with the kinds (or brands) of paper. However, those changing operations are troublesome, and the afore-mentioned optical conditions may change (without attracting the notice of the operator) even for the same brand of paper. Therefore, it has been difficult for the conventional moisture content meter to continuously measure the moisture content of paper with high accuracy.

SUMMARY OF THE INVENTION

Therefore, the present invention has been conceived to solve the problems thus far described, and the object thereof is to provide method and apparatus for accurately generating the signals corresponding to the moisture content of paper while eliminating the influences from the optical factors of the paper.

In order to attain the afore-mentioned object, the method and apparatus according to the present invention is characterized in that there are provided two optical systems having different degrees of interaction with paper, in that two kinds of photometric optical signals and two kinds of reference optical signals are detected through the respective optical systems, and in that those four signals are used to obtain the signals corresponding to the moisture content of paper.

DESCRIPTION OF THE PREFERRED EMBODIMENTS

The present invention will now be described in more detail in the following.

We have conducted precise analysis of the M/R signal-moisture content characteristics of the known moisture content meter, as shown in FIGS. 3 and 4, and have concluded that the factors, upon which the optical characteristics of the paper depend, are the base weight BW, the surface area A of fibers, the reflection factor r, the absorption coefficient $\alpha$, the specific volume V and the moisture weight MW. Here, the following relationships are known to hold between those variables and the number of layers n and the transmission factor f of the paper:

$$n = \tfrac{1}{2} \times BW \times A$$

$$f = e^{-\alpha \frac{V \times BW}{n}}$$

As in the above, the layer number n is a function of the base weight BW and the surface area A of the fibers, whereas the transmission factor f is a function of the absorption coefficient $\alpha$, the specific volume V, the base weight BW and the layer number n.

As a result, the variables determining the optical characteristics of paper can be restricted to the four variables, i.e., the layer number n, the transmission factor f, the reflection factor r and the moisture weight MW so that the M signals and the R signals can be expressed in the following forms:

$$M = F_m(MW, n, r, f)$$

$$R = F_r(n, r, f).$$

Here, the reason why the R signals are not the function of the moisture weight MW is because the reference light (having a wavelength of about 1.80 microns) is hardly influenced by the moisture content in the paper.

In the actual moisture content meter, the ratio between the M signals and the R signals is taken to compensate the instability in the components or elements of the meter, as has been described before. The resultant M/R signals are also the function of the afore-mentioned four variables, namely:

$$M/R = F_{m/r}(MW, n, r, f).$$

On the basis of the considerations thus far made, the characteristic curves of FIGS. 3 and 4 can be understood, as follows:

Between the GP paper and the BKP paper, the most prominent difference is found in the surface area A of the fibers among the afore-mentioned variables such that the GP paper has a value 2.0 to 2.5 times that of the BKP paper. As a result, it can be judged that the difference in the characteristic curves between the GP paper and the BKP paper results from the difference in the afore-mentioned surface area A of the fibers. More specifically, in the system having a high degree of interaction between the photometric and reference lights and the paper (or in the multiscattering type moisture content meter), the influences due to the surface area A of the fibers are so lightened that the GP paper and the BKP paper exhibit substantially the same characteristic. On the contrary, in the system having a low degree of interaction between the respective lights and the paper (or in the transmission type moisture content meter), the GP paper has a higher sensitivity than the BKP paper.

On the other hand, the characteristics of the fully bleached paper, the unbleached paper and the newsprint will be described in the following.

Among those papers, the most prominent difference is found in the transmission factor f among the afore-mentioned variables. For example, the bleached paper has a factor f higher than 0.990 whereas the unbleached paper and the news print have a factor ranging from 0.970 to 0.930. As a result, it can be judged that the differences in the characteristic curves among the bleached paper, the unbleached paper and the news print result from the difference in the afore-mentioned transmission factor f. In other words, less influences due to the difference in the transmission factor are found in the system having the lower degree of interaction between the photometric and reference lights and the paper.

From the above analysis, the following conclusion can be obtained.

If the system using the near infrared ray is so constructed that the signals, which are the function of the variables MW, n, r and f determining the optical characteristics of paper and which have different sensitivities to the respective variables, (which signals will be called the detection signals) can be generated, then the moisture weight MW can be determined from the correlations among those detection signals.

Here, the detection signals $I_1$, $I_2$, $I_3$ and $I_4$ are defined by the following Equations (1), (2), (3) and (4), respectively:

$$I_1 = F_1(MW, n, r, f) \quad (1)$$

$$I_2 = F_2(MW, n, r, f) \quad (2)$$

$$I_3 = F_3(MW, n, r, f) \quad (3)$$

$$I_4 = F_4(MW, n, r, f) \quad (4)$$

Although methods for generating the detections signals $I_1$ to $I_4$ can be conceived in various manners, it should be noted to obviate the calculations which are to be accomplished when the moisture weight MW is determined with the use of the detection signals generated. For example, the detection signals, which are generated by irradiating the paper with the beams having wavelengths $\lambda_1$, $\lambda_2$, $\lambda_3$ and $\lambda_4$ and by introducing the beams, which have conducted interactions with the paper, into the photosensitive element, can be handled to correspond to the afore-mentioned detection signals $I_1$ to $I_4$. If, however, the wavelengths $\lambda_1$ to $\lambda_4$ become remarkably different, the reflection factor r and the transmission factor f of the paper at each wavelength exhibit different values so that the calculations for determining the moisture weight MW become accordingly complex.

With these in mind, the present invention will take the following method.

Figure 5:
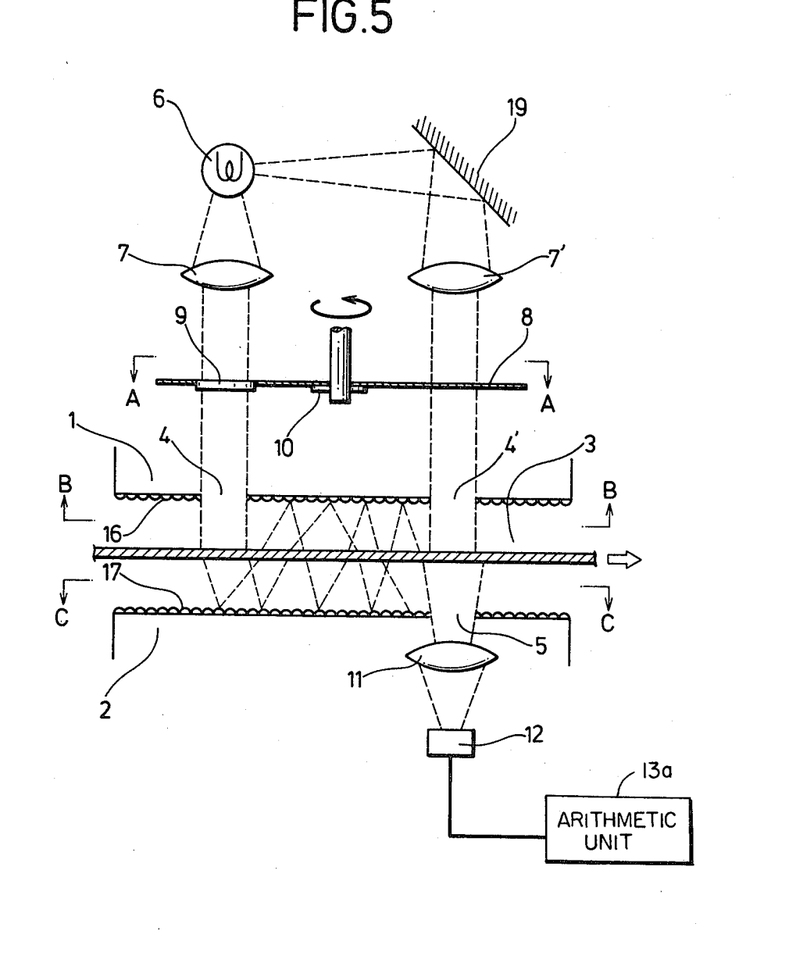
FIG. 5 is an explanatory view illustrating the construction of the detecting unit of the moisture content meter according to one embodiment of the present invention.

In FIG. 5 showing the construction of the moisture content meter according to one embodiment of the present invention, the upper and lower heads 1 and 2 are arranged to face each other and to have their facing surfaces formed with the reflecting coating layers 16 and 17. The upper head 1 is formed with two irradiation apertures 4 and 4', whereas the lower head 2 is formed with the incident aperture 5 which is positioned to face the irradiation aperture 4'. Moreover, there is disposed in the upper head 1 the rotary wheel 8, which is equipped with the photometric optical filter 10 and the reference optical filter 9 arranged on a common disc, so that the paper is irradiated with the interrupted lights, which come from the lamp 6, the lenses 7 and 7' and the reflecting mirror 19, by way of the irradiation apertures 4 and 4'. On the other hand, there is disposed in the lower head 2 a detecting system, which is composed of the lens 11 and the photosensitive element 12, so that the electric signals corresponding to the intensity of the incident light from the aperture 5 are fed to the arithmetic unit 13a of the subsequent stage.

The positional relationships among the afore-mentioned irradiation apertures 4 and 4', incident aperture 5 and rotary wheel 8 will be described in more detail in the following with reference to FIG. 6.

Figure 6A:
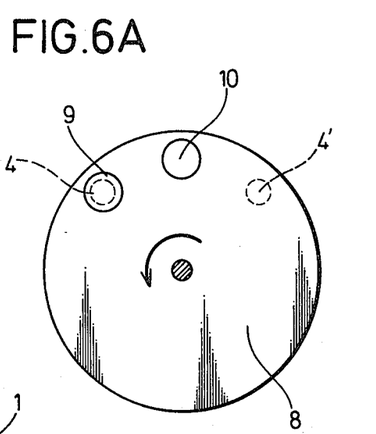
FIGS. 6A, 6B and 6C are construction explaining views taken along sections A—A, B—B and C—C.
Figure 6B:
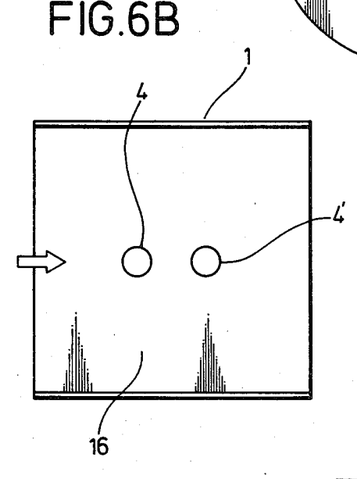
Figure 6C:
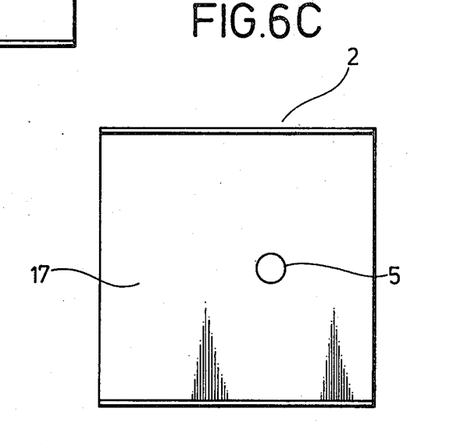
Figure 7:
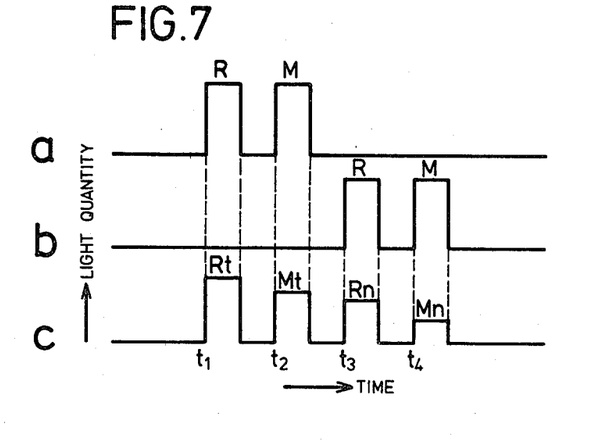
FIG. 7 is a timing chart illustrating the respective signals at the detecting unit having the construction of FIG. 5.
Figure 8A:
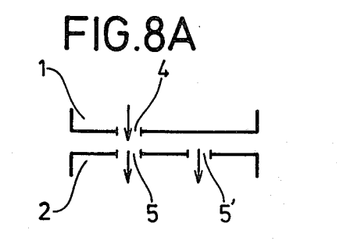
FIGS. 8A, 8B, 8C and 8D are explanatory views illustrating the constructions of the detecting units according to other embodiments of the present invention.
Figure 8B:
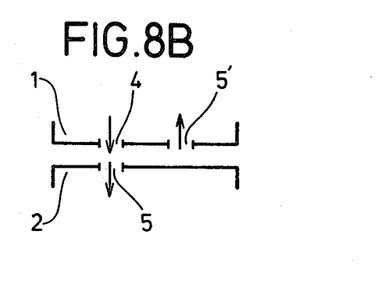
Figure 8C:
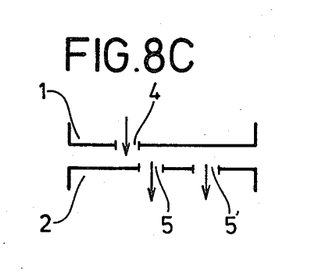
Figure 8D:
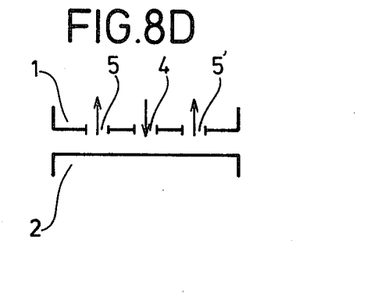

FIGS. 6A, 6B and 6C are construction explaining views taken along sections A—A, B—B and C—C of FIG. 5 (although the sizes are not necessarily made equal). The irradiation apertures 4 and 4' of the upper head 1 are arranged at a spacing in the direction of feed of the paper (or in the direction of arrow in FIG. 6B), and the incident aperture 5 is formed in the facing surface of the lower head 2 and arranged in alignment with the irradiation aperture 4' (as seen from FIG. 6C). On the other hand, the positional relationships among the through holes (in which the filters 9 and 10 are mounted) of the rotary wheel 8 which is mounted in the upper head 1 and the irradiation apertures 4 and 4' are determined such that, if the optical filter 9 or 10 comes to one of the optical paths relating to the irradiation apertures 4 and 4', the other optical path is shielded by the disc portion. In other words, the construction is made such that both the irradiation beams do not come from the irradiation apertures 4 and 4'. As a result, now, if the rotary wheel 8 is turned in the direction of arrow in FIG. 6A, then the respective filters consecutively intersect the optical paths formed by the respective irradiation apertures so that signals, as shown in the waveform a in FIG. 7, are generated from the irradiation aperture 4' whereas signals, as shown in the waveform b in FIG. 7, are generated from the irradiation aperture 4. As a result, the signals, as shown in the waveform c in FIG. 7, are introduced into the incident aperture 5. In FIG. 7 showing the respective waveforms, ordinate indicates the quantity of light whereas abscissa indicates the time lapse. In FIG. 7, moreover: waveform R denotes the signals by the optical filter 9; waveform M denotes the signals by the optical filter 10; waveforms $R_t$ and $M_t$ denote the signals incident upon the aperture 5 and coming from the aperture 4'; and waveforms $R_n$ and $M_n$ denote the signals incident upon the aperture 5 and coming from the aperture 4.

The sensitivities of the moisture weight MW, the layer number n, the transmission factor f and the reflection factor f to the afore-mentioned signals $R_t$, $M_t$, $R_n$ and $M_n$ are experimentally attained to have the relationship, as tabulated in Table 1:

TABLE 1

| Signal | Variable | | | |
|---|---|---|---|---|
| | MW | n | f | r |
| $R_t$ | Minimum | High | Low | Low |
| $M_t$ | Medium | High | Low | Low |
| $R_n$ | Minimum | Low | High | Low |
| $M_n$ | High | Low | High | Low |

As is apparent from Table 1, the signals $R_t$, $M_t$, $R_n$ and $M_n$ have different sensitivities to the respective variables. Incidentally, the reason why the signals $R_t$ and $R_n$ exhibit the minimum sensitivity to the moisture weight MW is because the reference light (having a wavelength of about 1.80 microns) has no absorptive characteristics to the moisture content.

Now, the detection signals, which are generated by introducing the aforementioned respective signals $R_t$, $M_t$, $R_n$ and $M_n$ into the photosensitive element 12, will be described in the following in connection with the detection signals $I_1$ to $I_4$ which are expressed by Equations (1) to (4). That is to say, the detection signals of $R_t$ are denoted at $I_1$; the detection signals of $M_t$ are denoted at $I_2$; the detection signals of $R_n$ are denoted at $I_3$; and the detection signals of $M_n$ are denoted at $I_4$.

These detection signals $I_1$ to $I_4$ are fed to the (not-shown) arithmetic unit of the subsequent step, and the desired arithmetic operations (or the simultaneous Equations (1) to (4) are solved) are performed so that the influences from the variables n, f and r can be eliminated to generate the signals corresponding only to the moisture weight MW. As is apparent from Table 1, incidentally, the reflection factor r is low for all the signals $R_t$, $M_t$, $R_n$ and $M_n$. If the influences are ignored, the signals to the arithmetic unit (if the reduction in the measuring accuracy is admitted) can be reduced to three with sufficient results so that the construction of the arithmetic unit can be accordingly simplified.

In the actual measurement, however, there is a case, in which all the afore-mentioned variables n, f and r are not factors for the errors (i.e., in which the influence of a variable can be ignored). In the moisture measurement of newsprint, for example, an error is established in accordance with the concentration of the newsprint (e.g., about 1% of error for 10% concentration of the newsprint). The cause for this error has been confirmed by our experiments to come from the transmission factor f (but not the layer number n which is substantially at such a constant level as to constitute no cause for the error). In the case thus far described, signals $I_1'$ and $I_2'$ based on Equations (5) and (6) are produced, and the desired arithmetic operations are performed by the arithmetic unit so that the moisture content signals set free from the influence of the transmission factor f can be generated:

$$I_1' = I_3/I_1 = R_n/R_t \quad (5);$$

$$I_2' = I_4/I_3 = M_n/R_n \quad (6).$$

In accordance with the brand of paper, moreover, there may arise a case, in which the layer number n establishes the causes for the error. In this case, the afore-mentioned signals $I_2'$ and the signals $I_3'$ based on Equation (7) are also used, and the desired arithmetic operations are performed in the arithmetic unit so that the moisture content signals set free from the influence of the layer number n can be generated:

$$I_3' = I_2/I_1 = M_t/R_t \quad (7).$$

Incidentally, even if the inverse numbers of the signals $I_1'$, $I_2'$ and $I_3'$ based upon Equations (5), (6) and (7) are used for accomplishing the afore-mentioned calculations, it is likewise possible to generate the moisture content signals from which the influences of the transmission factor f and the layer number n are eliminated.

Other embodiments of the present invention will now be described in the following.

FIGS. 8A, 8B, 8C and 8D show the constructions of the upper and lower heads and illustrate the positional relationships between the irradiation aperture 4 and the incident apertures 5 and 5' of the upper and lower heads 1 and 2.

In FIGS. 8A, 8B, 8C and 8D, the beam containing the photometric wavelength light and the reference wavelength light is introduced as an interrupted light from the irradiation aperture 4 into the (not-shown) article to be measured so that the photometric and reference lights are separated and detected from the lights incident upon the apertures 5 and 5'. As a result, two kinds of the M signals and two kinds of R signals are generated (by the respective optical systems having the same fundamental constructions as those shown in FIG. 2). In the constructions shown in FIGS. 8A and 8B, the irradiation aperture 4 has its optical axis aligned with that of the incident aperture 5 but not (or offset from) with that of the incident aperture 5'. As a result, the signals $R_t$ and $M_t$ can be generated from the light which has been incident upon the aperture 5, and the signals $R_n$ and $M_n$ are generated from the light which has been incident upon the aperture 5'. In the constructions shown in FIGS. 8C and 8D, moreover, the optical axes of the incident apertures 5 and 5' are spaced (or offset) from that of the irradiation aperture 4 with the different quantities of offset. As a result, the quantities of the incident lights upon the apertures 5 and 5' are not equal. Consequently, the signals $R_n$, $M_n$, $R_n'$ and $M_n'$ based upon the respective incident lights (wherein: the signals $R_n$ and $M_n$ come from the incident lights upon the aperture 5; and the signals $R_n'$ and $M_n'$ come from the incident lights upon the aperture 5') exhibit different values, and the respective signals can be deemed as the signals corresponding to the signals $I_1$ to $I_4$, as expressed by the Equations (1) to (4).

In the constructions of FIG. 8, incidentally, although the facing surfaces of the upper and lower heads are not formed with the reflecting coating films, the present invention does not necessarily require such reflecting coating films but can attain the same resultant effects as is equipped with the reflecting coating film if the facing surfaces of the upper and lower heads are finished to have mirror surfaces.

As has been described hereinbefore in detail, since the signals corresponding to the moisture content in the paper can be accurately generated while compensating the influences from the optical factors of the paper, the present invention can enjoy the remarkable effects in the relevant field.

What is claimed is:

1. A method of measuring the moisture contained or absorbed in a sheet of paper by irradiating the sheet of paper with near infrared radiation having a first wavelength which is more absorbed by the moisture and a reference wavelength which is less absorbed by the moisture, detecting said first and reference wavelengths after the radiation has interacted with the paper, and processing signals indicative of the detected radiation in a predetermined arithmetic operation, wherein the improvement comprises the steps of:

providing first and second optical systems having different path lengths between an irradiation aperture through which the sheet of paper can be irradiated with said near infrared radiation and an incident aperture through which the radiation having interacted with the sheet of paper can be received; and processing in a predetermined arithmetic operation, detected signals Mt and Rt which are dependent on said first wavelength and said reference wavelength, respectively, in said first optical system, and detected signals Mn and Rn which are dependent on said first wavelength and said reference wavelength, respectively, in said second optical system, for deriving a moisture content signal free from the influence of the optical properties of the sheet of paper.

2. A method according to claim 1, in which said first and second optical systems are of the transmission type and of the multi-scattering type, respectively, and the detected signals Mt and Rt are dependent on said first wavelength and said reference wavelength, respectively, in said transmission-type optical system, and the detected signals Mn and Rn are dependent on said first wavelength and said reference wavelength, respectively, in said multi-scattering-type optical system, said signals being used to derive an Mn/Rn signal or an Rn/Mn signal, and an Rn/Rt signal or Rt/Rn signal, said Mn/Rn signal and Rn/Rt signal, or said Rn/Mn signal and Rt/Rn signal being used to effect a predetermined arithmetic operation for deriving a moisture content signal free from the influence of a transmission factor f of said sheet of paper.

3. A method according to claim 1, in which said first and second optical systems are of the transmission type and of the multi-scattering type, respectively, and the detected signals Mt and Rt are dependent on said first wavelength and said reference wavelength, respectively, in said transmission-type optical system, and the detected signals Mn and Rn are dependent on said first wavelength and said reference wavelength, respectively, in said multi-scattering-type optical system, said signals being used to derive an Mn/Rn signal or an Rn/Mn signal, and an Mt/Rt signal or Rt/Mt signal, said Mn/Rn signal and Mt/Rt signal, or said Rn/Mn signal and Rt/Mt signal being used to effect a predetermined arithmetic operation for deriving a moisture content signal free from the influence of a layer number n of said sheet of paper.

4. An apparatus for measuring the moisture contained or absorbed in a sheet of paper, including a head comprising an irradiation unit with a chamber having a first irradiation aperture in a sidewall thereof and housing a radiation source for emitting infrared radiation having a first wavelength which is absorbed by the moisture in said paper and a reference wavelength which is less absorbed by the moisture, and a detection unit with a chamber having a first incident aperture in a sidewall thereof and housing therein a photosensitive element, said sidewall of said detection unit being disposed in confronting relation to said sidewall having the first irradiation aperture, or a head comprising an irradiation and detection unit having a chamber with a first irradiation aperture in a sidewall thereof and a first incident aperture housing a source of radiation for emitting infrared radiation of a first wavelength which is absorbed by the moisture in said paper and a reference wavelength which is less absorbed by the moisture and also housing a photosensitive element, a reflective member disposed in confronting relation to said sidewall having said first irradiation and incident apertures; and an arithmetic unit receptive of input signals dependent on said first wavelength and reference wavelength as detected by said photosensitive element when the sheet of paper passes through a clearance defined between said irradiation unit and said detection unit of the head or a clearance defined between said irradiation and detection unit and said reflective member of the head, for processing the received signals in a predetermined arithmetic operation to derive a signal indicative of the moisture contained or absorbed in the sheet of paper, said head having a second irradiation aperture or a second incident aperture, said first irradiation aperture and said second incident aperture or said second irradiation aperture and said first incident aperture jointly constituting a second optical system having a radiation path length different from that of a first optical system constituted jointly of said first irradiation aperture and said first incident aperture, said arithmetic unit being receptive of detected signal inputs Mt and Rt dependent respectively on said first wavelength and said reference wavelength in said first optical system and detected signals Mn and Rn dependent respectively on said first wavelength and said reference wavelength in said second optical system.

* * * * *